United States Patent
Tsujiuchi et al.

(10) Patent No.: US 8,415,502 B2
(45) Date of Patent: Apr. 9, 2013

(54) METHOD AND APPARATUS FOR PRODUCING MONO-LOWER-ALKYL MONOALKANOLAMINE

(75) Inventors: Tatsuya Tsujiuchi, Hiroshima (JP); Shinya Tachibana, Hiroshima (JP); Tsuyoshi Oishi, Hiroshima (JP); Tomio Mimura, Hyogo (JP); Yasuyuki Yagi, Hyogo (JP); Hidehisa Mita, Kanagawa (JP); Ryosuke Araki, Kanagawa (JP); Kenji Saito, Kanagawa (JP)

(73) Assignees: Mitsubishi Heavy Industries, Ltd., Tokyo (JP); The Kansai Electric Power Co., Inc., Osaka-shi, Osaka (JP); Nippon Nyukazai Co., Ltd., Tokyo (JP)

( * ) Notice: Subject to any disclaimer, the term of this patent is extended or adjusted under 35 U.S.C. 154(b) by 0 days.

(21) Appl. No.: 12/994,599

(22) PCT Filed: Oct. 24, 2008

(86) PCT No.: PCT/JP2008/069340
§ 371 (c)(1),
(2), (4) Date: Nov. 24, 2010

(87) PCT Pub. No.: WO2009/144848
PCT Pub. Date: Dec. 3, 2009

(65) Prior Publication Data
US 2011/0071318 A1    Mar. 24, 2011

(30) Foreign Application Priority Data
May 26, 2008   (JP) .................................. 2008-137278

(51) Int. Cl.
*C07C 213/04* (2006.01)
(52) U.S. Cl. ...................................... 564/477; 564/475
(58) Field of Classification Search .................... 564/477
See application file for complete search history.

(56) References Cited

U.S. PATENT DOCUMENTS

| 6,703,478 B2 | 3/2004 | Nakane et al. |
| 7,977,513 B2 * | 7/2011 | Tachibana et al. ............ 564/477 |
| 2003/0220529 A1 | 11/2003 | Nat et al. |

FOREIGN PATENT DOCUMENTS

| JP | 59-13751 A | 1/1984 |
| JP | 61-186341 A | 8/1986 |
| JP | 2000-204065 A | 7/2000 |
| JP | 2002-249470 A | 9/2002 |
| JP | 2004-223426 A | 8/2004 |
| JP | 2004-275933 A | 10/2004 |
| JP | 2005-520828 A | 7/2005 |
| JP | 2007-217344 A | 8/2007 |
| JP | 2007-277200 A | 10/2007 |
| WO | 01/83582 A1 | 11/2001 |
| WO | 03/078360 A1 | 9/2003 |

OTHER PUBLICATIONS

Database CAPLUS on STN, Acc. No. 2008:1140122, Gu et al., CN 101265195 A (Sep. 17, 2008) (abstract).*
Written Opinion of the International Searching Authority of International Application No. PCT/JP2008/069340, date Oct. 2, 2009.
International Search Report of PCT/JP20081069340, date of mailing dated Feb. 10, 2009.
Oda, Ryohei et al.; "Surfactant"; Maki Shoten, 1965, pp. 262-263. (partial English translation).

* cited by examiner

*Primary Examiner* — Brian J Davis
(74) *Attorney, Agent, or Firm* — Westerman, Hattori, Daniels & Adrian, LLP

(57) ABSTRACT

A reaction column (12) to which a raw material mixture (11) containing a mono-lower-alkylamine (AA: raw material I) and an alkylene oxide (AO: raw material II) is supplied, an unreacted raw material distillation column (14) that separates an unreacted raw material (15) from a reaction product (13*a*) (containing the unreacted raw material (15), a target reaction product (monomer) (17), and a by-product (dimer) (18)), and a flash drum (16) to which a reaction product (13*b*) (containing the target reaction product (monomer) (17) and the by-product (dimer) (18)) is supplied, the flash drum (16) separating a mono-lower-alkyl monoalkanolamine (monomer, the target reaction product 17) in a gas state, are provided.

3 Claims, 4 Drawing Sheets

METHOD AND APPARATUS FOR PRODUCING MONO-LOWER-ALKYL MONOALKANOLAMINE

TECHNICAL FIELD

The present invention relates to a method and an apparatus for producing a mono-lower-alkyl monoalkanolamine having high commercial demand, in which the mono-lower-alkyl monoalkanolamine is obtained by a reaction of a mono-lower-alkylamine with an alkylene oxide.

BACKGROUND ART

Mono-lower-alkyl monoalkanolamines are compounds having high commercial demand and useful as intermediate materials in general organic synthesis, such as medical and agrochemical intermediates and intermediates of cationic flocculants, etching solutions for resins, softeners for synthetic fibers, corrosion inhibitors, neutralizers for petroleum refining and petroleum processing, and dispersants.

Production of a mono-lower-alkyl monoalkanolamine by a reaction of a mono-lower-alkylamine with an alkylene oxide has already been reported in literatures (for example, Non-Patent Document 1).

In the reaction of a mono-lower-alkylamine with an alkylene oxide, a mono-lower-alkyl monoalkanolamine and a mono-lower-alkyl dialkanolamine are produced simultaneously. To selectively obtain the mono-lower-alkyl monoalkanolamine in this reaction, a significantly excessive amount of mono-lower-alkylamine used must be used when compared with the amount of alkylene oxide used. Therefore, with this reaction, a large amount of mono-lower-alkylamine remains unreacted.

As a method for producing a mono-lower-alkyl monoalkanolamine by a reaction of a mono-lower-alkylamine with an alkylene oxide, a zeolite catalyst method that uses zeolite as a catalyst is proposed (Patent Document 1).

Conversely, as a method that does not use the zeolite catalyst, for example, a production method performed under supercritical conditions (temperature condition: 100 to 200° C., pressure condition: 17 to 24 MPa) is proposed (Patent Document 2).

As a method for producing a mono-lower-alkyl monoalkanolamine by a reaction of a mono-lower-alkylamine with an alkylene oxide, a production method in which the reaction is performed in the presence of water is well known (this production method is referred to as a water catalyst method).
Non-Patent Document 1: Ryohei Oda and Kazuhiro Teramura, "Surfactant," Maki Shoten, 1965, p. 262 to 263.
Patent Document 1: Japanese Patent Application Laid-Open No. 2004-275933
Patent Document 2: Japanese Patent Application Laid-Open No. Sho 59-13751

DISCLOSURE OF INVENTION

Problem to be Solved by the Invention

In the "zeolite catalyst method" disclosed in Patent Document 1, a chiller must be used in a condenser in a distillation column for separating an unreacted raw material (raw material I), and this causes a problem of an increase in energy consumption.

In the "supercritical method" disclosed in Patent Document 2, the temperature condition must be 100 to 200° C., and the pressure condition must be 17 to 24 MPa. This causes a problem of an increase in power and cost necessary for operation.

To improve the yield of the mono-lower-alkyl monoalkanolamine in the water catalyst method described above, the molar ratio of the alkylene oxide to the mono-lower-alkylamine must be low. In this case, since the mono-lower-alkylamine is used cyclically, the reboiler load in the distillation column increases, and this causes a problem of an increase in energy consumption. In addition, a large amount of water separated by distillation in a refining system must be subjected to wastewater treatment, and this causes a problem of an increase in cost.

One common problem in the zeolite catalyst method and the water catalyst method is that, when a monomer is mass-produced, the mass production cost may increase because additional cost for disposal of a dimer, which is a by-product, is required.

Therefore, there is a desperate demand for a mono-lower-alkyl monoalkanolamine producing method and apparatus that can reduce the production cost and wastewater treatment cost even in mass production and achieve good cost efficiency.

In view of the foregoing problems, the present invention provides a mono-lower-alkyl monoalkanolamine producing method and apparatus that can produce a mono-lower-alkyl monoalkanolamine with reduced production cost and reduced wastewater treatment cost.

Means for Solving Problem

According to an aspect of the present invention, a method for producing a mono-lower-alkyl monoalkanolamine by a reaction of a mono-lower-alkylamine (AA) with an alkylene oxide (AO) includes: supplying the mono-lower-alkylamine (AA) and the alkylene oxide (AO) to a reaction column and reacting the mono-lower-alkylamine (AA) with the alkylene oxide (AO) to synthesize the mono-lower-alkyl monoalkanolamine and then removing an unreacted raw material by distillation; and separating the mono-lower-alkyl monoalkanolamine in a gas state in a flash drum.

Advantageously, in the method for producing a mono-lower-alkyl monoalkanolamine, an operating temperature of the flash drum is in a range of 110 to 200° C.

Advantageously, in the method for producing a mono-lower-alkyl monoalkanolamine, the reaction for synthesis is a water catalyst method.

According to another aspect of the present invention, an apparatus for producing a mono-lower-alkyl monoalkanolamine by a reaction of a mono-lower-alkylamine with an alkylene oxide includes: a reaction column in which the mono-lower-alkylamine (AA) and the alkylene oxide (AO) supplied thereto are reacted to synthesize the mono-lower-alkyl monoalkanolamine; a distillation column in which an unreacted raw material is removed by distillation; and a flash drum in which the mono-lower-alkyl monoalkanolamine in a gas state is recovered.

Advantageously, in the apparatus for producing a mono-lower-alkyl monoalkanolamine, an operating temperature of the flash drum is in a range of 110 to 200° C.

Advantageously, in the apparatus for producing a mono-lower-alkyl monoalkanolamine, the reaction for synthesis is a water catalyst method.

Effect of the Invention

According to the present invention, a flash drum is provided so that a mono-lower-alkyl monoalkanolamine in a gas state is separated. This can simplify a separating step of separating a dimer, which is a by-product, by distillation, and the production cost of the mono-lower-alkyl monoalkanolamine can thereby be reduced.

Figure 1:
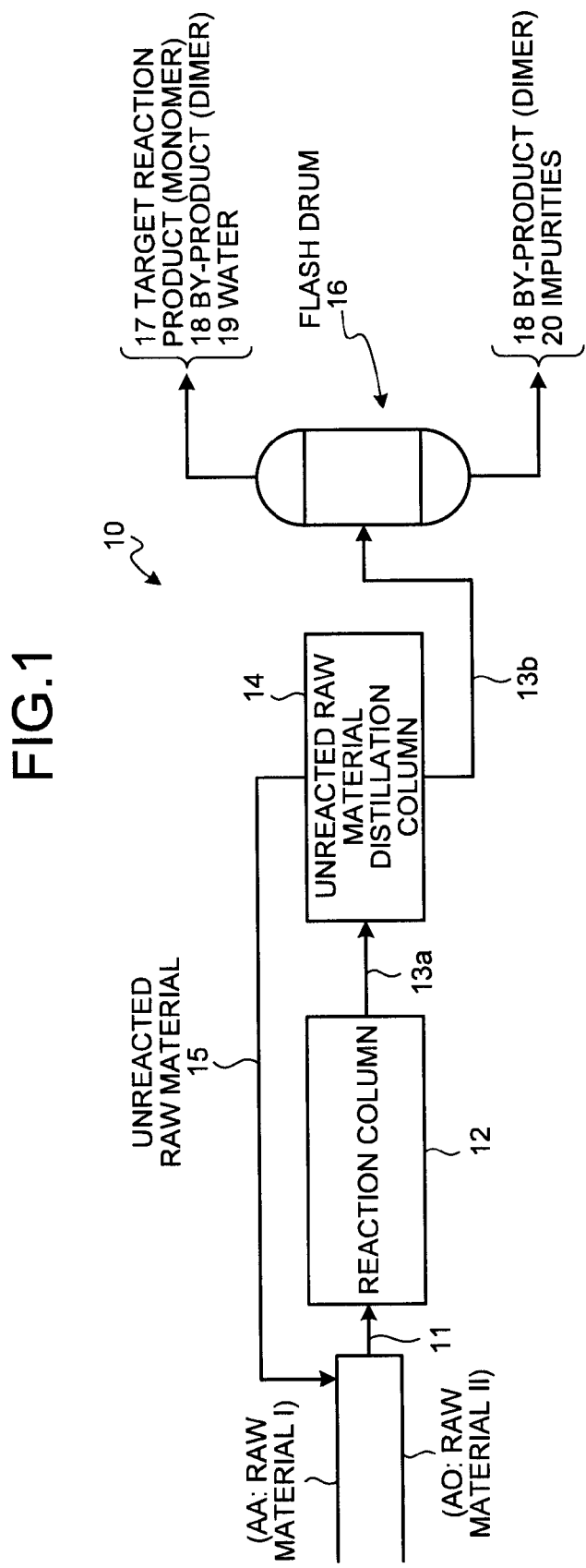
FIG. 1 is a schematic diagram illustrating a mono-lower-alkyl monoalkanolamine producing apparatus according to an embodiment.

EXPLANATIONS OF LETTERS OR NUMERALS 10 mono-lower-alkyl monoalkanolamine producing apparatus
11 raw material mixture
12 reaction column
13a, 13b reaction product
14 unreacted raw material distillation column
15 unreacted raw material
16 flash drum
17 target reaction product (monomer)
18 by-product (dimer)
19 water
20 impurities

BEST MODE FOR CARRYING OUT THE INVENTION

Hereinafter, the present invention will be described in detail with reference to the drawings. However, the present invention is not limited to an embodiment described below. The components in the embodiment include those readily apparent to persons skilled in the art and those substantially similar thereto.

Embodiment

A mono-lower-alkyl monoalkanolamine producing method according to an embodiment of the present invention will be described with reference to the drawings.

FIG. 1 is a schematic diagram illustrating the mono-lower-alkyl monoalkanolamine producing apparatus according to the embodiment.

As shown in FIG. 1, the mono-lower-alkyl alkanolamine producing apparatus 10 according to the embodiment includes: a reaction column 12 to which a raw material mixture 11 containing a mono-lower-alkylamine (AA: raw material I) and an alkylene oxide (AO: raw material II) is supplied; an unreacted raw material distillation column 14 that separates an unreacted raw material 15 from a reaction product 13a (containing the unreacted raw material 15, a target reaction product (monomer) 17, and a by-product (dimer) 18); and a flash drum 16 to which a reaction product 13b (containing the target reaction product (monomer) 17 and the by-product (dimer) 18) from which the unreacted raw material 15 has been removed is supplied, the flash drum 16 separating a mono-lower-alkyl monoalkanolamine (monomer) being the target reaction product 17 in a gas state.

The monomer in a gas state separated in the flash drum 16 is cooled by a cooling apparatus (not shown) to be in a liquid state.

The cooled product is formed mainly of the target reaction product (monomer) 17 but contains the by-product (dimer) 18 and water 19.

The dimer being the by-product 18 and impurities 20 in a liquid state are discharged from the bottom of the flash drum 16 to be treated separately.

In the present invention, the mono-lower-alkyl monoalkanolamine may be produced in the reaction column 12 under the conditions of a temperature in the range of, for example, 40 to 300° C. The temperature range is preferably 50 to 200° C. and particularly preferably 50 to 150° C. The operating pressure may be, for example, 0.1 to 20 MPa, preferably 0.1 to 15 MPa, and particularly preferably 3.0 to 10 MPa.

No particular limitation is imposed on the mono-lower-alkylamine (AA) being the raw material I used in the present invention. Example of the usable mono-lower-alkylamine include linear and branched monoalkylamines having 1 to 6 carbon atoms such as monomethylamine, monoethylamine, mono-n-propylamine, monoisopropylamine, mono-n-butylamine, monoisobutylamine, mono-sec-butylamine, mono-t-butylamine, mono-n-pentylamine, isopentylamine, and mono-n-hexylamine. Monomethylamine, monoethylamine, mono-n-propylamine, monoisopropylamine, mono-n-butylamine, monoisobutylamine, and mono-t-butylamine can be preferably used. Monomethylamine, monoethylamine, mono-n-propylamine, monoisopropylamine, and mono-n-butylamine can be particularly preferably used.

No particular limitation is imposed on the alkylene oxide (AO) being the raw material II used in the present invention. Alkylene oxides having 2 to 4 carbon atoms such as ethylene oxide, propylene oxide, and butylenes oxide can be preferably used. Ethylene oxide and propylene oxide can be particularly preferably used.

In a water catalyst method in the present invention, the concentration of water in the raw materials supplied to the reaction column 12 is preferably in the range of 1 to 40 percent by weight. The range of the concentration of water is preferably 5 to 30 percent by weight and particularly preferably 5 to 20 percent by weight.

In the production of the mono-lower-alkyl monoalkanolamine by the water catalyst method in the present invention, the reaction rate varies depending on the concentration of water. The higher the concentration of water is, the higher the reaction rate becomes, and this condition is more preferable.

In the present invention, the supply ratio of the raw materials is specified. More specifically, the molar ratio of the mono-lower-alkylamine raw material to the alkylene oxide raw material (alkylene oxide raw material I)/mono-lower-alkylamine raw material II) is in the range of preferably 0.05 to 0.5 and more preferably 0.1 to 0.3.

If the molar ratio exceeds 0.5, although the reboiler load in the unreacted raw material recovering distillation column 14 for recovering the unreacted raw material 15 is reduced, the reaction time increases, which is not preferred. If the molar ratio is less than 0.05, although the reaction time can be reduced, the reboiler load increases significantly, which is also not preferred.

As described above, in the present embodiment, the reaction product 13b from which the unreacted raw material 15 has been removed is supplied to the flash drum 16, and the mono-lower-alkyl monoalkanolamine in a gas state is separated in the flash drum 16. In this manner, the separating step of separating the dimer being a by-product 18 by distillation can be simplified, and the production cost of the mono-lower-alkyl monoalkanolamine is thereby reduced.

Therefore, wastewater treatment of the separated water that is required when a distillation column is used is not required, and the cost efficiency is thereby improved.

Since the dimer being a by-product is mixed into the target product, the incineration cost of the dimer, which is conventionally treated separately, is reduced.

In the water catalyst process, the operating temperature of the flash drum 16 is in the range of preferably 110 to 190° C. and more preferably 130 to 170° C. Preferably, the operating pressure is set such that the dimer can be separated as a liquid in these operating temperature ranges.

The reason that the upper limit of the operating temperature is set to 190° C. is as follows. If the operating temperature exceeds 190° C., the monomer and dimer may deteriorate, which is not preferred. If the operating temperature is less than 110° C., the monomer and dimer may not be well separated.

Figure 2:
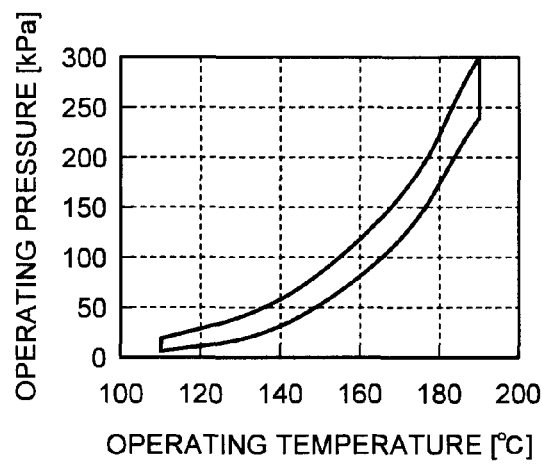
FIG. 2 is a graph showing the relationship between the operating conditions (temperature and pressure) of a flash drum.

FIG. 2 is a graph showing the relationship between the operating temperature and the operating pressure.

Figure 3:
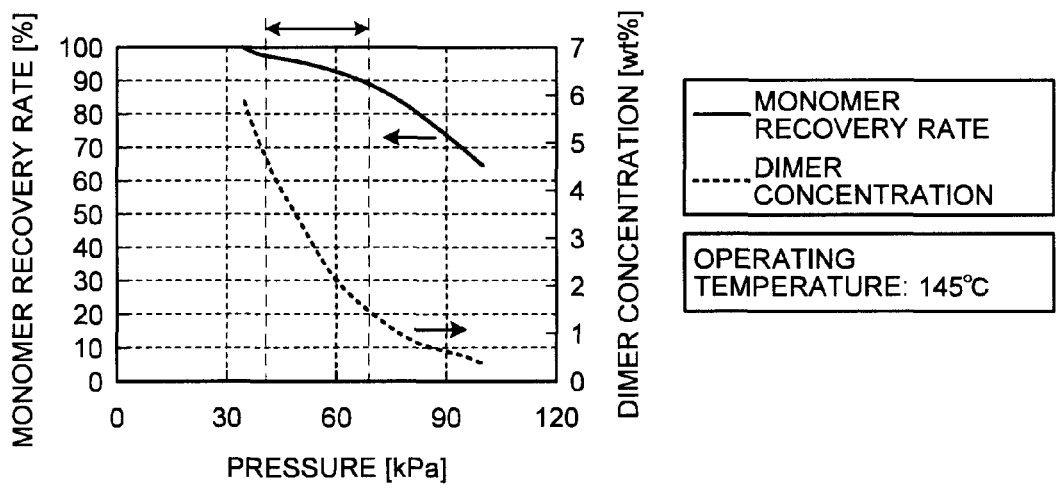
FIG. 3 is a graph showing the relationship between the pressure and the recovery rate of a monomer.

FIG. 3 shows an example of the relationship between the operating pressure and the recovery rate of the monomer.

In the example shown in FIG. 3, the operating temperature is 145° C. In this case, it is preferable to set the operating pressure in the range of 40 to 70 kPa. As the pressure increases, the amount of monomer recovered from the upper portion of the flash drum decreases. Therefore, the upper limit of the operating pressure is set such that the recovery rate of the monomer is 90% or higher.

As described above, in the mono-lower-alkyl monoalkanolamine producing apparatus according to the present embodiment, the reaction is performed in the reaction column 12, and then the unreacted raw material 15 is separated in the unreacted raw material distillation column 14. Then, the monomer and the dimer are not separated by distillation, supplied to the flash drum 16, and the system causes a release in pressure. In this manner, the monomer being the target reaction product 17 in a gas state is recovered from the top portion of the flash drum 16, and at the same time the by-product 18 and the impurities 20 in a liquid state are separated in the bottom portion. Accordingly, the production cost of the mono-lower-alkyl monoalkanolamine can be reduced.

Preferably, the amount of the dimer contained in the gas is 5 percent by weight or less.

In the process of the water catalyst method, a large amount of water is used in the reaction in the reaction column 12. This is preferable because the reboiler amount can be significantly reduced, but the present invention is not limited thereto. As shown in a Test Example described later, when a nonaqueous zeolite method is used in the reaction in the reaction column 12, the reboiler amount can be reduced.

Examples of the catalyst used in the zeolite catalyst method include ZSM-5, which is known as a synthetic zeolite. The ZSM is an abbreviation of Zeolite of Socony Mobil, which is the name of a company that developed the synthetic zeolite. Examples the zeolite catalyst having an MEL structure include ZSM-11 also known as a synthetic zeolite. In the present invention, it is preferable to use zeolite, and ZSM-5 is particularly preferably used.

When the catalyst is used, the reaction is performed in a nonaqueous system. Therefore, when the raw material I is supplied as an aqueous solution (for example, water content: 40%), a nonaqueous distillation column must be separately provided to remove water in advance.

In the zeolite method, the flash drum 16 is operated under the conditions of preferably 120 to 200° C. because no water is present. At these operating temperatures, the operating pressure is set such that the dimer can be separated as a liquid. For example, at 120° C., the operating pressure may be in the range of 6 to 12 kPa. For example, at 200° C., the operating pressure may be in the range of 170 to 194 kPa.

Test Example 1

Hereinafter, the present invention will be described more specifically using Test Examples, but the present invention is not limited thereto.

Figure 4:
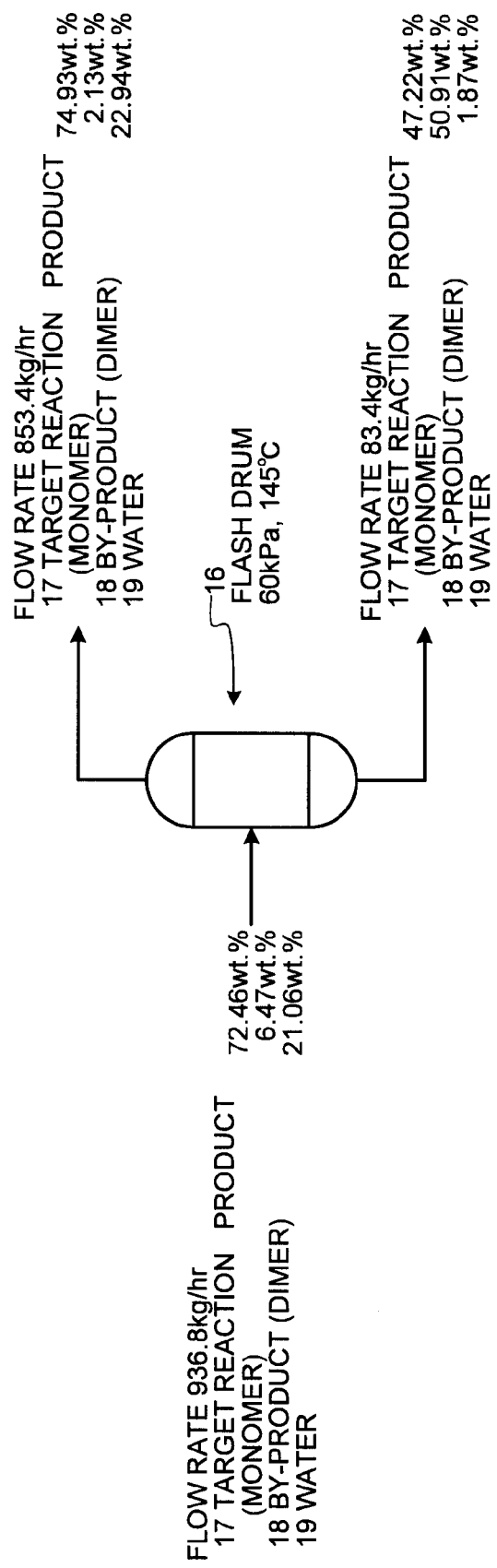
FIG. 4 is a schematic diagram of a mono-lower-alkyl monoalkanolamine producing apparatus in Test Example 1.

A mono-lower-alkyl monoalkanolamine producing apparatus 10 having the same structure as that in the embodiment shown in FIG. 1 was used. The reaction was performed in the reaction column 12, and the reaction product 13b from which the unreacted raw material 15 had been separated by distillation was supplied to the flash drum 16. The reaction was performed by the water catalyst method. The reaction conditions are shown in FIG. 4 and below.

(Reaction Product Supplied to Flash Drum 16)

Operating temperature: 145° C. (pressure: 60 kPa)

Concentration of the target reaction product (monomer) 17 supplied to the flash drum 16: 72.46 percent by weight Concentration of the by-product (dimer) 18 supplied to the flash drum 16: 6.47 percent by weight Concentration of water 19 supplied to the flash drum 16: 21.06 percent by weight Flow rate of these materials: 936.8 kg/hr (Reaction Product Discharged from Top Portion of the Flash Drum 16)

Operating temperature: 145° C. (pressure: 60 kPa)

Concentration of the target reaction product (monomer) 17 discharged from the top portion of the flash drum 16: 74.93 percent by weight Concentration of the by-product (dimer) 18 discharged from the top portion of the flash drum 16: 2.13 percent by weight Concentration of water 19 discharged from the top portion of the flash drum 16: 22.94 percent by weight Flow rate of these materials: 853.4 kg/hr (Reaction Product Discharged from Bottom Portion of Flash Drum 16)

Concentration of the target reaction product (monomer) 17 discharged from the bottom portion of the flash drum 16: 47.22 percent by weight Concentration of the by-product (dimer) 18 discharged from the bottom portion of the flash drum 16: 50.91 percent by weight Concentration of water 19 discharged from the bottom portion of the flash drum 16: 1.87 percent by weight Flow rate of these materials: 83.4 kg/hr In the above case, the reboiler amount was reduced by 42.5%.

Test Example 2

Figure 5:
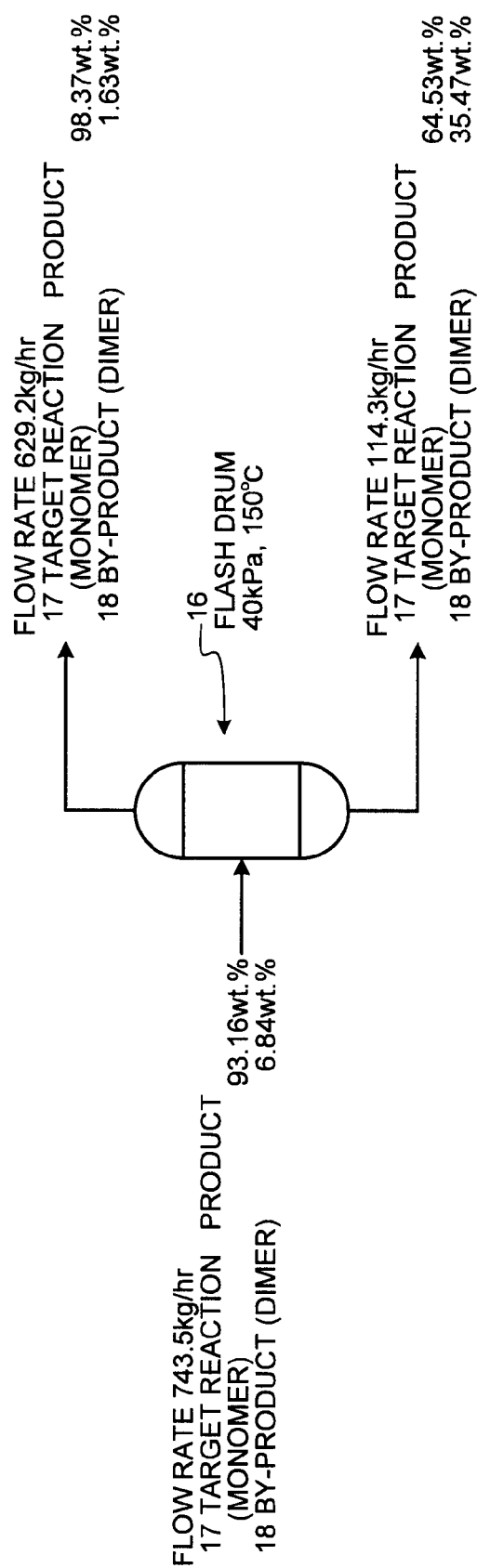
FIG. 5 is a schematic diagram of a mono-lower-alkyl monoalkanolamine producing apparatus in Test Example 2.

A mono-lower-alkyl monoalkanolamine producing apparatus 10 having the same structure as that in the embodiment shown in FIG. 1 was used. The reaction was performed in the reaction column 12, and the reaction product 13b from which the unreacted raw material 15 had been separated by distillation was supplied to the flash drum 16. The reaction was performed by the zeolite catalyst method. The reaction conditions are shown in FIG. 5 and below.

(Reaction Product Supplied to Flash Drum 16)

Operating temperature: 150° C. (pressure: 40 kPa)

Concentration of the target reaction product (monomer) 17 supplied to the flash drum 16: 93.16 percent by weight Concentration of the by-product (dimer) 18 supplied to the flash drum 16: 6.84 percent by weight Flow rate of these materials: 743.5 kg/hr (Reaction Product Discharged from Top Portion of the Flash Drum 16)

Concentration of the target reaction product (monomer) 17 discharged from the top portion of the flash drum 16: 98.37 percent by weight Concentration of the by-product (dimer) 18 discharged from the top portion of the flash drum 16: 1.63 percent by weight Flow rate of these materials: 629.2 kg/hr (Reaction Product Discharged from Bottom Portion of Flash Drum 16)

Concentration of the target reaction product (monomer) 17 discharged from the bottom portion of the flash drum 16: 64.53 percent by weight Concentration of the by-product (dimer) 18 discharged from the bottom portion of the flash drum 16: 35.47 percent by weight Flow rate of these materials: 114.3 kg/hr In the above case, the reboiler amount was reduced by 3.6%.

INDUSTRIAL APPLICABILITY

As described above, in the mono-lower-alkyl monoalkanolamine producing method and apparatus of the present invention, it is not necessary to actively separate water and the dimer during production of the mono-lower-alkyl monoalkanolamine. Therefore, the mono-lower-alkyl monoalkanolamine can be produced at low cost.

The invention claimed is:

1. A method for producing a mono-lower-alkyl monoalkanolamine by a reaction of a mono-lower-alkylamine (AA) with an alkylene oxide (AO), comprising:

supplying the mono-lower-alkylamine (AA) and the alkylene oxide (AO) to a reaction column and reacting the mono-lower-alkylamine (AA) with the alkylene oxide (AO) to synthesize the mono-lower-alkyl monoalkanolamine and then removing an unreacted raw material by distillation; and separating the mono-lower-alkyl monoalkanolamine in a gas state in a flash drum.

2. The method for producing a mono-lower-alkyl monoalkanolamine according to claim 1, wherein an operating temperature of the flash drum is in a range of 110 to 200° C.

3. The method for producing a mono-lower-alkyl monoalkanolamine according to claim 1, wherein the reaction for synthesis is a water catalyst method.

* * * * *